(12) United States Patent
Vilar et al.

(10) Patent No.: US 12,062,229 B2
(45) Date of Patent: Aug. 13, 2024

(54) IDENTIFICATION PROCESS OF A DENTAL IMPLANT VISIBLE ON AN INPUT IMAGE BY MEANS OF AT LEAST ONE CONVOLUTIONAL NEURAL NETWORK

(71) Applicant: ADVENTIVE, Saint-Mandé (FR)

(72) Inventors: Denis Vilar, Saint-Mandé (FR); Alexis Vilar, Saint Foy d'Aigrefeuille (FR)

(73) Assignee: ADVENTIVE, Saint-Mandé (FR)

( * ) Notice: Subject to any disclaimer, the term of this patent is extended or adjusted under 35 U.S.C. 154(b) by 534 days.

(21) Appl. No.: 17/387,983

(22) Filed: Jul. 28, 2021

(65) Prior Publication Data
US 2022/0036105 A1 Feb. 3, 2022

(30) Foreign Application Priority Data
Jul. 28, 2020 (FR) ........................................ 2007966

(51) Int. Cl.
*G06V 10/94* (2022.01)
*G06T 7/00* (2017.01)
(Continued)

(52) U.S. Cl.
CPC ............ *G06V 10/95* (2022.01); *G06T 7/0014* (2013.01); *G06V 10/25* (2022.01); *G16H 30/40* (2018.01);
(Continued)

(58) Field of Classification Search
CPC .... G06V 10/95; G06V 10/25; G06V 2201/03; G06T 7/0014; G06T 2207/20084; G06T 2207/30036; G06T 2207/30052
See application file for complete search history.

(56) References Cited

U.S. PATENT DOCUMENTS

2017/0340418 A1* 11/2017 Raanan ................ G06V 30/142
2018/0108124 A1   4/2018 Guo et al.
(Continued)

FOREIGN PATENT DOCUMENTS

DE      112018005089 T5    6/2020
KR         101811644 B1 * 12/2017
WO     WO-2019204520 A1 * 10/2019 ........... A61B 5/4547

OTHER PUBLICATIONS

Sukegawa S, Yoshii K, Hara T, Yamashita K, Nakano K, Yamamoto N, Nagatsuka H, Furuki Y. Deep Neural Networks for Dental Implant System Classification. Biomolecules. Jul. 1, 2020;10(7):984. doi: 10.3390/biom10070984. PMID: 32630195; PMCID: PMC7407934. (Year: 2020).*
(Continued)

*Primary Examiner* — Bobbak Safaipour
*Assistant Examiner* — Ashley L. Hytrek
(74) *Attorney, Agent, or Firm* — Thomas | Horstemeyer, LLP (57) ABSTRACT

The invention relates to a process for identification of an implant, optionally worn by an individual, comprising the following steps, performed by a processing unit:
obtaining a radiographic input image in which a dental implant is visible;
classification of a region of interest of said radiographic image by means of at least one convolutional neural network; said classification producing a list of candidate implants to be the implant visible on the image, the list being ordered as a function of a probability of being the implant visible on the image.

11 Claims, 8 Drawing Sheets

(51) Int. Cl.
*G06V 10/25* (2022.01)
*G16H 30/40* (2018.01)

(52) U.S. Cl.
CPC ............... *G06T 2207/10116* (2013.01); *G06T 2207/20081* (2013.01); *G06T 2207/20084* (2013.01); *G06T 2207/30036* (2013.01); *G06T 2207/30052* (2013.01); *G06V 2201/03* (2022.01)

(56) References Cited

U.S. PATENT DOCUMENTS

| 2019/0303712 | A1* | 10/2019 | Suprono | ................ G06F 18/28 |
| 2019/0332896 | A1 | 10/2019 | Liang et al. | |
| 2020/0074631 | A1 | 3/2020 | Giancardo et al. | |

OTHER PUBLICATIONS

Jiao Licheng et al: 11 a Survey on the New Generation of Deep Learning in Image Processing, IEEE Access, vol. 7, Nov. 28, 2019 (Nov. 28, 2019), pp. 172231-172263, XP011759131, DOI: 10.1109/Access.2019.2956508 [extrait le Dec. 6, 2019].

* cited by examiner

| Image | Radiographic image | Score | Brand | Model |
|---|---|---|---|---|
| | | 90.48% | Nobel Biocare | Replace Select Tapered |
| | | 82.25% | Nobel Biocare | Nobel Replace Tapered |
| | | 69.38% | Camlog | Root-Line (J-Series) |
| | | 67.18% | Steri-Oss | Steri-Oss Replace Select |

FIG. 10

IDENTIFICATION PROCESS OF A DENTAL IMPLANT VISIBLE ON AN INPUT IMAGE BY MEANS OF AT LEAST ONE CONVOLUTIONAL NEURAL NETWORK

CROSS-REFERENCE TO RELATED APPLICATIONS

This application claims priority to French Application Number 2007966, filed on Jul. 28, 2020, and entitled "Procédé d'identification d'un implant dentaire visible sur une image d'entrée au moyen d'au moins un réseau de neurones à convolution," which is incorporated herein by reference in its entirety.

GENERAL TECHNICAL FIELD

The invention relates to the identification of a dental implant visible on an input image and relates in particular to a process for identification of such an implant by means of at least one convolutional neural network as well as a learning process of the convolution neural network or networks involved.

PRIOR ART

Many different models of dental implants are placed worldwide. Unfortunately the traceability of each implant is not always well documented, such that when they have to take action on an implant, dental surgeons do not necessarily know which implant it is, in particular when they did not place the implant originally.

This is problematic in the event where practitioners are confronted with biological or prosthetic complications and each implant model operates with specific pieces. Therefore, without the exact references of the implant, it often proves impossible to know which screwdriver or which part to use to carry out treatment.

Currently, identification of dental implants is done manually based on the specialist knowledge of an expert or by searching in a database.

This manual research is laborious and not without risk because either the expert does not know all the implants or the database is not utilized properly or does not correctly describe the implants it contains.

There is therefore a need to be able to identify a dental implant on a radiographic image as precisely as possible.

PRESENTATION OF THE INVENTION

The invention identifies a dental implant, optionally worn by an individual, from a radiographic image in which the implant is visible.

For this purpose, the invention proposes a process for identification of a dental implant, optionally worn by an individual, comprising the following steps, performed by a processing unit:
  obtaining a radiographic input image in which a dental implant is visible;
  classification of a region of interest of said radiographic image by means of at least one convolutional neural network; said classification producing a list of candidate implants to be the implant visible on the image, the list being ordered as a function of a probability of being the implant visible on the image.

The invention is advantageously completed by the following characteristics, taken singly or in any one of their technically possible combinations:
  classification comprises a detection step of a region of interest of the radiographic image by means of a first trained neural network and a trimming step of the radiographic image according to this region of interest;
  classification comprises a determination step of a representative vector by means of a third trained neural network, said representative vector describing the radiographic image optionally trimmed according to the region of interest;
  classification comprises a comparison step of the representative vector determined at a set of representative reference vectors corresponding to reference implants obtained during a learning step of the third neural network so as to obtain a set of scores of similarities, each score characterizing a distance of the representative vector determined at each representative reference vector;
  classification comprises a determination step of at least one probability of corresponding to a technical characteristic specific to an implant, each probability being determined by means of a second neural network;
  classification comprises a comparison step of each probability of corresponding to a technical characteristic specific to an implant with a set of technical characteristic reference implants so as to obtain a correspondence score for each reference implant;
  the process comprises a determination step from all the scores of similarities and/or the correspondence score associated with each reference implant, of a set of final scores associated with each reference implant, each score quantifying the correspondence between the implant visible on the image and each reference implant and constituting the list of candidate implants;
  the reference implants originated from a database of implants optionally filtered as a function of contextual data such as for example the origin of the implant, the year of construction, the form of connection;
  the process comprises a learning step of at least one neural network from a database of annotated data and radiographic reference images, said database of annotated data comprising references of the reference implants and the coordinates of reference regions of interest of radiographic reference images, said learning for identifying on the reference images a region of interest and technical characteristics specific to each reference implant visible on each reference image and vectors representative of each reference image;
  the learning step of at least one neural network comprises a step for augmenting data consisting of applying to each radiographic reference implant image at least one random transformation from the following transformations: rotation, trimming, enlarging, modification of brightness, modification of contrast, mirror, perspective, noise;
  the learning step comprises the learning of the first neural network from the database of annotated data such that the first neural network is configured to determine coordinates of a region of interest containing said implant for a radiographic reference image in which an implant is visible;
  the learning step comprises the learning of the third neural network from the database of annotated data such that the third neural network is configured to determine a representative vector describing the radiographic image;

the learning step comprises the learning of an entire second neural network from the database of annotated data such that each neural network of the entire second neural network is configured to determine a probability of corresponding to a technical characteristic specific to an implant;

the learning step of the entire second neural network and of the third neural network comprises a step for trimming the reference images according to the identified regions of interest;

the learning step of the entire second neural network and of the third neural network comprises a resampling step so as to ensure that the technical characteristics specific to each implant are fairly represented.

The invention also relates to a computer program product comprising code instructions for the execution of a process according to the invention, when said program is run on a computer.

PRESENTATION OF THE FIGURES

Other characteristics, aims and advantages of the invention will emerge from the following description which is purely illustrative and non-limiting and which must be considered with respect to the appended drawings, in which.

In all figures similar elements bear identical reference numerals.

DETAILED DESCRIPTION

Architecture

Figure 1:
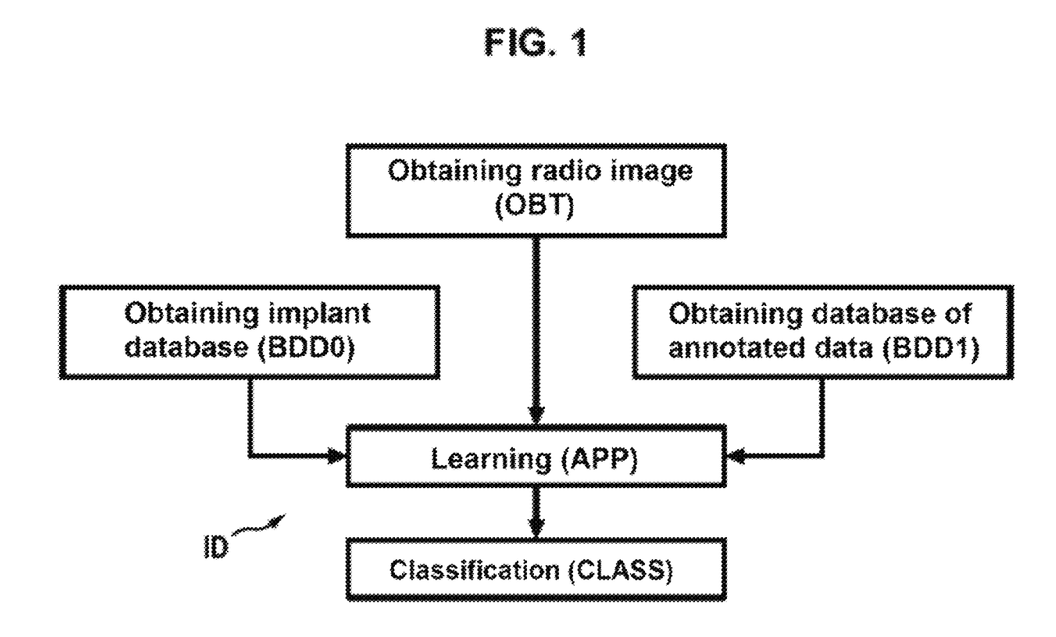
FIG. 1 illustrates steps of a process for identification of a dental implant according to an embodiment of the invention.

In the following, as illustrated in FIG. 1 several aspects associated with an identification process ID of a dental implant, optionally worn by an individual, will be described:

classification CLASS of an input image in which a dental implant is visible, the dental implant being optionally worn by an individual, classification being carried out by means of at least one neural network;

learning APP of each neural network.

Figure 2:
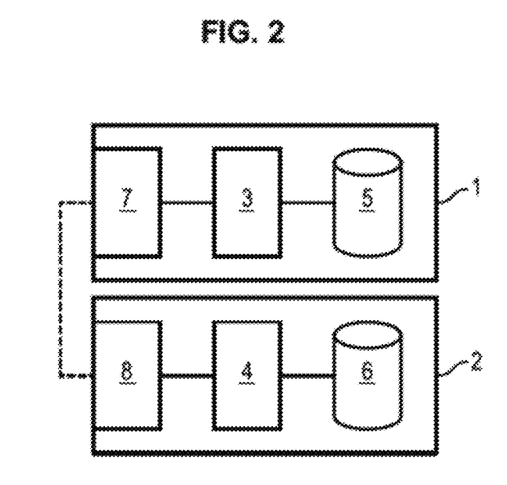
FIG. 2 illustrates an example of architecture for implementation of the invention.

These steps are performed within an architecture such as illustrated in FIG. 2.

The learning process APP can be carried out on a first server 1 and the classification process CLASS can be carried out on a second server 2. Each server 1, 2 advantageously comprises at least one processing unit 3, 4, for example a graphics processor (Graphics Processing Unit, (GPU)) preferably having high calculation power. Such a type of processing unit produces high calculation speeds especially for learning APP relative to more conventional processing units.

Each server 1, 2 can also comprise a communications interface 7, 8 enabling mutual communication. Such communication can for example be executed by means of a wired or wireless link by means of any type of communications network, for example the Internet network. With respect to the first server 1, it can have access by means of the communications interface 7 to one or more remote databases useful for learning.

By way of advantage also, each server 1, 2 can comprise a storage unit 5, 6, a hard drive for example. Typically, the first learning server 1 can store in the storage unit 5 one or more databases serving as learning or have access to this database or these databases. The architecture can be advantageously completed by a live memory (Random Access Memory (RAM)) which stores intermediate calculations during learning.

The skilled person will easily understand that other architectures for executing the processes are possible, the two servers 1,2 capable especially of being combined.

Neural Network

Classification (step CLASS) employs at least one neural network previously trained during learning (step APP).

Neural networks are used extensively for classifying data.

After an automatic learning phase (generally supervised, that is, on a reference database of already classified data), a neural network "learns" and becomes capable of applying the same classification to unknown data.

Convolutional neural networks, or CNN (Convolutional Neural Networks) are a type of neural network wherein the connection pattern between the neurones is inspired by the visual cortex of animals. They are particularly adapted to a particular type of classification which is image analysis, where in fact they allow efficient recognition of objects or people in images or videos.

The Identification Process of a Dental Implant Worn by an Individual

FIG. 1 schematically illustrates steps of an identification process ID of a dental implant worn by an individual.

This process ID comprises a step for obtaining a database of dental implants $BDD_0$ and a database of annotated radiographic images $BDD_1$.

The process also comprises a learning step APP employing the database of annotated radiographic images $BDD_1$ and a classification step CLASS of a radiographic image on which a dental implant is visible. The dental implant can be worn by the individual or not.

This classification obtains one or more candidate dental implants to be the implant visible on the radiographic image. In addition to one or more trained neural networks, classification implements the database of annotated radiographic images $BDD_1$ and the database of dental implants $BDD_0$.

In the event where several candidates are obtained, the latter are presented in the form of a list of candidate implants, preferably ordered, as a function of a score determined during classification. In fact, classification quantifies a probability of correspondence of each candidate implant with the implant visible on the radiographic image.

It is on this basis that a practitioner wanting to identify an implant carries out its identification.

In practice, the practitioner provides the process for identification ID with a radiographic image on which the dental implant to be identified is visible.

Figure 3:
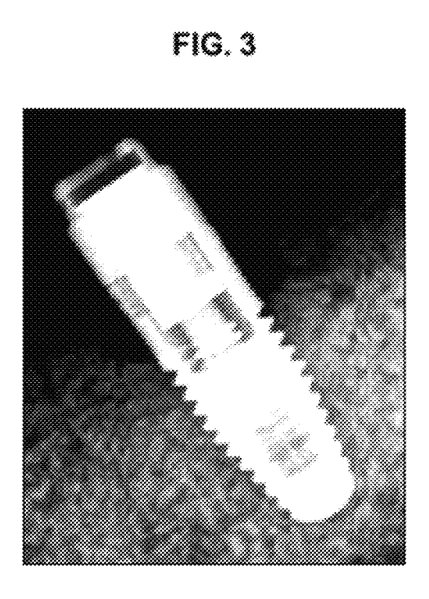
FIG. 3 illustrates an image of a dental implant executed in the invention.

It is noted that such a radiographic image (an example of which is illustrated in FIG. 3) is obtained (step OBT) by any means known per se for obtaining such an image. In particular, it can be obtained by means of X-ray equipment. Obtaining (step OBT) the radiographic image will not be detailed here as it is familiar to the skilled person.

Database of Implants $BDD_0$

Identifying the implant employs a database of implants $BDD_0$. This database comprises dental implant characteristics.

Figure 4:
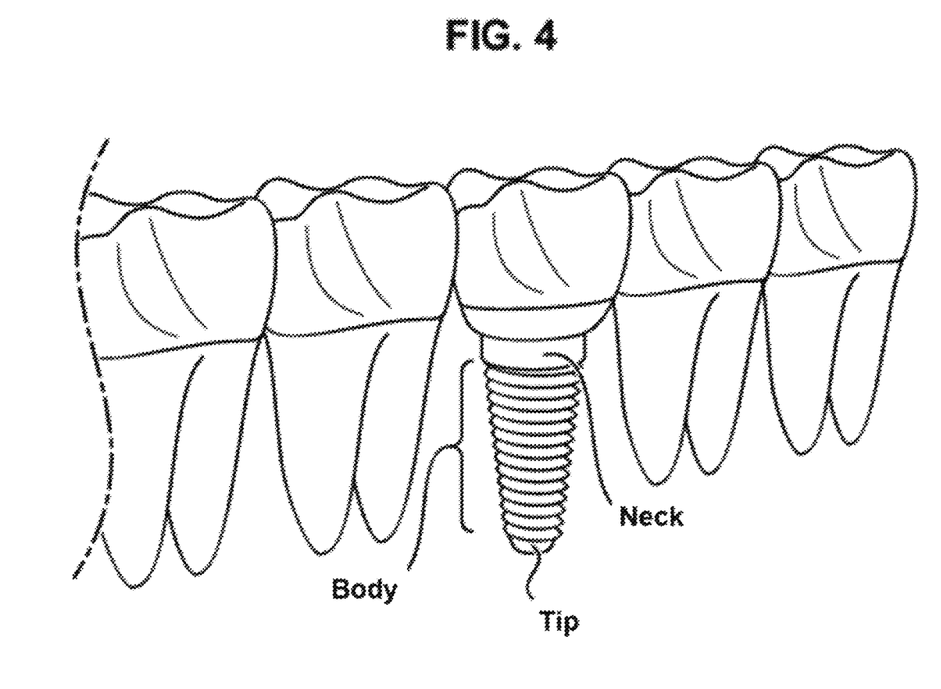
FIG. 4 illustrates a structure of a dental implant.

FIG. 4 schematically illustrates a dental implant (here worn by an individual). From top to bottom, a dental implant comprises a neck, a body and a tip. These three main elements define the geometry of the implant.

Associated with these geometric characteristics, a dental implant can also be characterized by other characteristics as well as by data called "metadata" comprising data on the country of distribution, the year it was first marketed, the origin and year of construction of the implant. Of course, this list of metadata is not exhaustive and can be completed.

The applicant has accordingly built a database of implants $BDD_0$ from all these characteristics. In particular, the database of implants $BDD_0$ references several brands of implants.

Such a database can for example comprise several different brands of implants, each brand proposing different implants.

For each model of implant the database of implants includes the following technical characteristics specific to each implant:
general characteristics:
type: standard, zygomatic, basal, short, narrow;
region of embedding: in the region of the bone, in the region of the tissue;
characteristics linked to the neck of an implant:
type of connection: external, internal, external/internal combination;
form of the connection: hexagon, octagon, monobloc, custom, triangle, square, pentagon, dodecagon, tri-lobe, four lobes, five lobes, six lobes, eight lobes, etc.;
form of the neck: wide, flared, straight, inclined;
micro-threading: yes or no;
characteristics linked to the body of the implant:
form of the body: conical, straight, conical tip;
threading of the body: none, isometric, square, saw tooth, inverted saw tooth;
characteristics linked to the tip:
form of the tip: conical, rounded flat, flared;
hole at the tip: none, round, oval;
grooves at the tip: or not.
characteristics linked to the origin of the implant:
year first marketed;
country of distribution.

These characteristics are the same for each model of implant.

Of course, a certain number of characteristics is being presented here, but other technical characteristics can be obtained while remaining within the framework of the processes described here.

Database of Annotated Radiographic Images $BDD_1$

To obtain the database of annotated radiographic images (hereinbelow database of annotated data $BDD_1$), a large number of radiographic reference images (for example, several thousand radiographic images) is collected and manually annotated with the corresponding reference of the implant.

Figure 5:
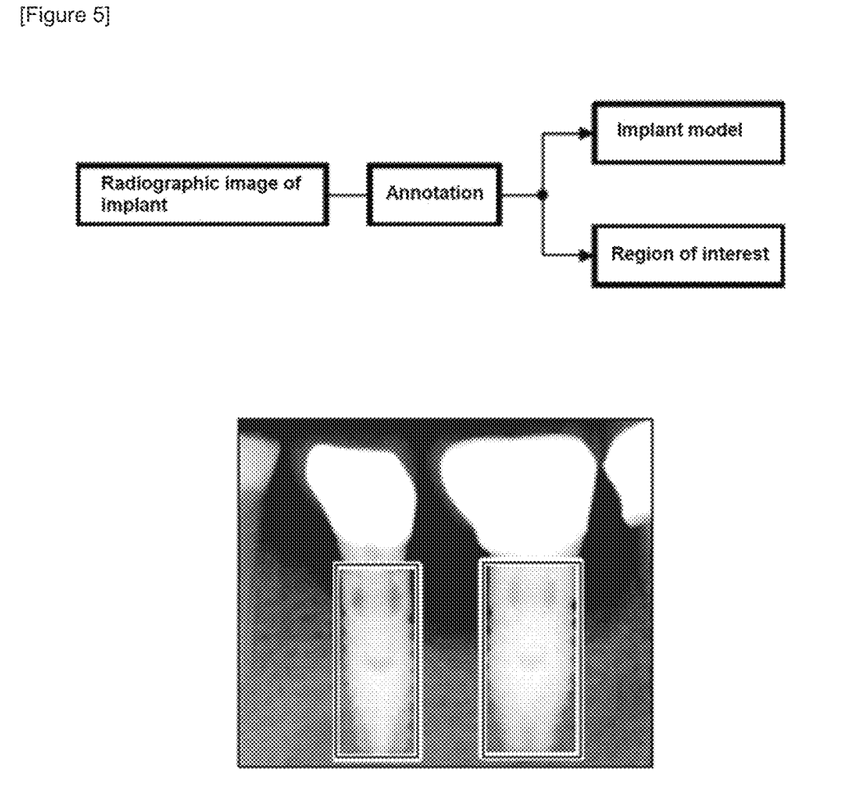
FIG. 5 illustrates steps for obtaining a database of annotated radiographic images used in the invention.

FIG. 5 illustrates the obtaining of the database of annotated data $BDD_1$. For each radiographic implant image the reference of the implant is filled out in the database of annotated data $BDD_1$. Associated with this reference, the coordinates of the box containing the implant (bounding box) are also filled out (white square in the radiographic image of FIG. 5). The bounding box is a region of interest used by the learning process and is advantageously defined by means of coordinates x, y, w, h, x and y as being the coordinates of the point at top left of the bounding box; w is the width of the box and h is the height of the box.

In this way, for each radiographic reference image the model of visible implant as well as the region of interest are filled out and stored.

This is about obtaining field truths utilized during learning.

It is understood that the database of annotated data $BBD_1$, is associated with an element of the database of implants $BDD_0$. But all the implants of the database of implants $BDD_0$ do not necessarily have associated images and are therefore not listed in the database of annotated radiographic images $BDD_1$. In other words, the database of annotated data $BDD_1$ references a subset of the database of implants $BDD_0$.

The Learning Process

As already mentioned, the learning of at least one neural network is carried out from the database of annotated data $BDD_1$. This learning trains neural networks so that on radiographic reference images they can serve to identify a region of interest (where the implant is located) and technical characteristics specific to each reference implant visible on each reference image.

Figure 6:
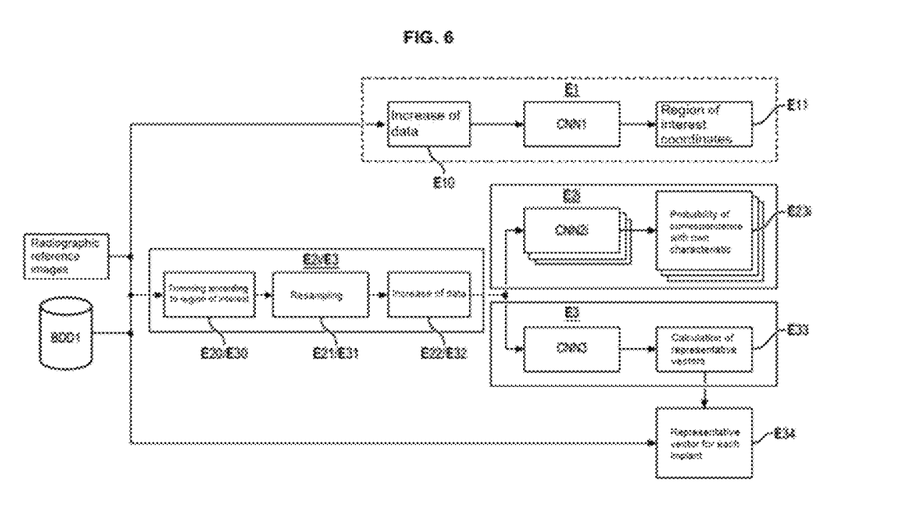
FIG. 6 illustrates steps of a learning process of one or more neural networks according to an embodiment of the invention.

FIG. 6 illustrates a learning process of at least one neural network according to an embodiment of the invention.

Such a process inputs radiographic reference images as well as the database of annotated data ($BDD_1$) and trains a first neural network CNN1, one or more second neural networks CNN2$i$ (with i the index designating the second neural network) and a third neural network CNN3.

Training of the First Neural Network CNN1

Learning (step E1) of the first neural network CNN1 is performed from radiographic reference images and the database of annotated data BDD1 such that for a given radiographic reference image in which an implant is visible, the first trained neural network CNN1 is configured to determine coordinates of a region of interest containing the reference (and therefore known) implant (step E11).

This first neural network CNN1 is for example a profound convolutional neural network. This here concerns dedicating this first neural network CNN1 to detecting a simple implant. Neural network architecture of Mask R-CNN type can be utilized. In this way, reference can be made to the article He K., Gkioxari G., et al.: "Mask R-CNN". Such a neural network is a known network for detecting zones in an image. In addition, learning the first neural network comprises a step for augmenting data (step E10). This step consists of applying various transformations to the radiographic reference images to heighten the diversity concerning the possibilities for obtaining the image.

The augmentation of the data permits to
augment the number of learning data;
allow the algorithm to better generalize new images (in particular by avoiding the phenomenon of over-learning);

better supports images obtained under different conditions (brightness, cropping, etc.).

The transformation can be applied to each image or just to some images. Transformation is for example rotation of the image, trimming of the image (truncation, cropping), enlarging, modification of brightness, modification of contrast, obtaining a mirror image, modification of perspective, sound effects (that is, a degradation) of the image.

Figure 7:
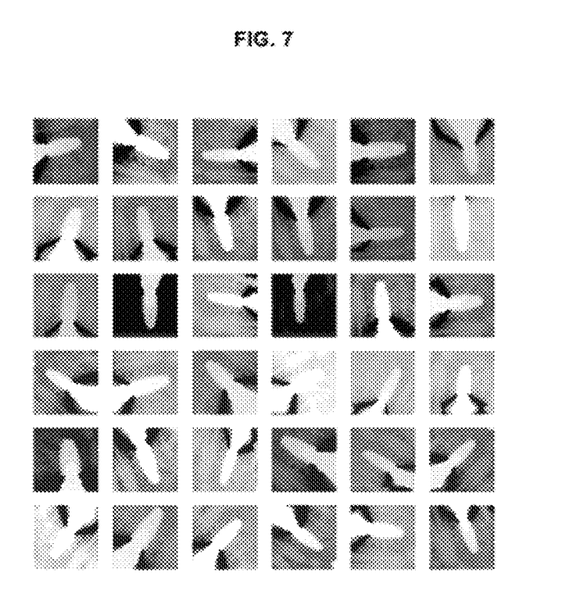
FIG. 7 illustrates an augmentation in data applied to a radiographic image of an implant according to an embodiment of the invention.

FIG. 7 illustrates 36 images obtained from the same image. The 36 images have been obtained by having various transformations applied to the same radiographic image of the same implant.

Training of Each Second Neural Network CNN2$i$

Learning each second neural network CNN2$i$ (step E2$i$) is done from radiographic reference images and the database of annotated data BDD$_1$ such that each second neural network CNN2$i$ is configured to determine a probability of corresponding to a technical characteristic specific to a reference implant.

Such a neural network is for example based on architecture of a profound convolutional neural network of the DenseNet network type, version 169. In light of this, reference can be made to the document Huang G., van der Maatern L. et al.: "Densely Connected Convolutional Networks". Another type of neural network can be of Inception V3 type. In this respect, reference can be made to the article Szegedy C., Vanhoucke V. et al.: "Rethinking the Inception Architecture for Computer Vision". Another type of neural network can be of ResNet type. In this respect, reference can be made to the article He K., Zhang X. et al.: "Deep Residual Learning for Image Recognition").

Each neural network can therefore forecast a technical characteristic specific to a reference implant (step E23$i$). For example, a number i=1 to 20 of neural networks is trained for each technical characteristic i, each comprising several classes.

The intrinsic technical characteristics are the characteristics presented hereinabove to describe the database of implants.

By way of example, the $i^{th}$ second neural network CNN2$i$ dedicated to the technical characteristic "form of the body" inputs a radiographic reference image and provides at output a vector of dimension 3 containing the probabilities associated with each "conical", "straight", "tip conical" class.

Training each second neural network CNN2$i$ can comprise a trimming step (step E20) of each radiographic reference image, a resampling step (step E21), a step for augmenting data (E22).

Steps E20, E21 and E22 can be performed all together, or not.

This describes a neural network for each characteristic but a single second neural network can be utilized to provide all the technical characteristics specific to each implant. In this case, a neural network called multi-tasking is utilized ("Multi-task learning").

The interest in having this second neural network or all these second neural networks is that this identifies any implant listed in the database of implants BDD$_0$ (that is, for which technical characteristics are available) without necessarily having annotated radiographic images (cf. BBD$_1$).

But it is noted that those implants having the same technical characteristics will have the same score and it will therefore be impossible to distinguish them. It is therefore understood that the combination with the third neural network CNN3 is more robust (hereinbelow).

Training of the Third Neural Network CNN3

Learning the third neural network CNN3 (step E3) is done from radiographic reference images and the database of annotated data BDD1 such that the third neural network CNN3 is configured to determine a representative vector (embedding) describing the radiographic reference image.

This is about training a neural network to calculate the similarity between two images of an implant. In the end this determines the similarity between two radiographic images of implants by calculating the distances between their representative vectors. The images of the same model of implant will be visually similar and will have close representative vectors, whereas the images of models of a different implant will have dissimilar representative vectors.

The third neural network is a profound convolutional learning neural network, for example. The similarity is here calculated directly from image to image without having to use technical characteristics coming from the second neural network or neural networks (CNN2$i$).

By way of advantage, for each reference image the third neural network CNN3 obtains a vector of fixed dimension (for example, comprising between 300 and 600 parameters). Each representative vector for each reference image is calculated so that the reference images of the same implant have close representative vectors, while those of different implants have distant representative vectors. In particular, a "Euclidian" distance type or "cosine similarity" type can be defined to define a distance between two representative vectors.

These representative vectors are otherwise called a signature of each radiographic reference image of reference implant.

The training of the third neural network CNN3 is based on architectures of neural networks utilized for facial recognition. A network of FaceNet type can be utilized. In this respect, reference can be made to the document Schroff F., Kalenichenko et al.: "FaceNet: A unified Embedding for Face Recognition and Clustering".

Figure 8:
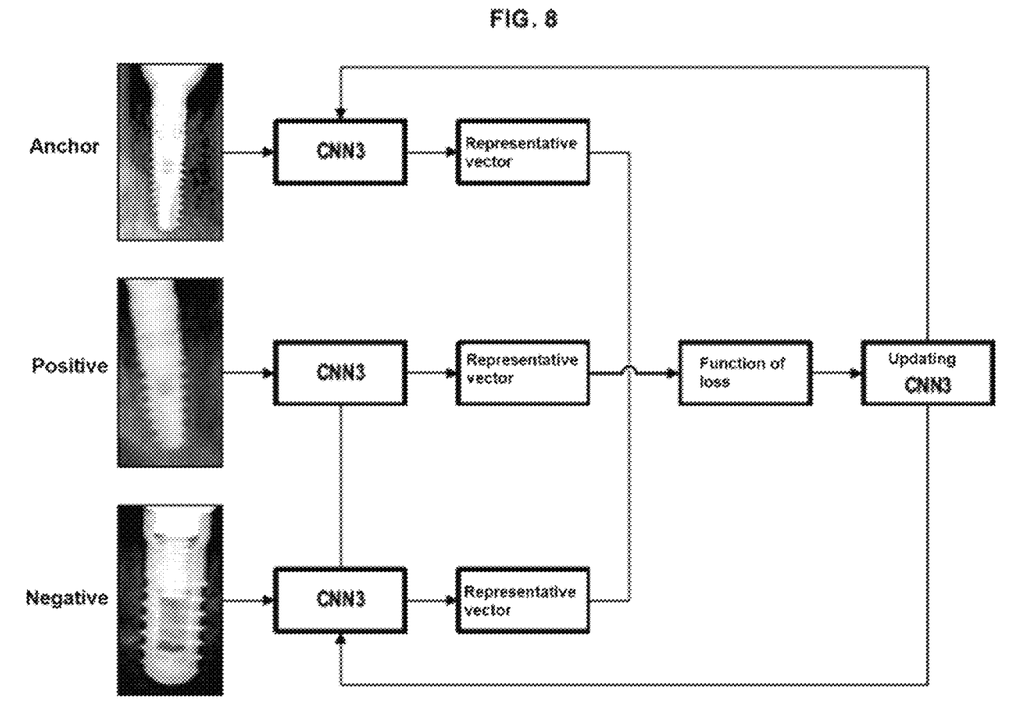
FIG. 8 illustrates steps for learning a third neural network according to an embodiment of the invention.

The training process of the third neural network can be summarized as follows, with the following steps performed iteratively in relation to FIG. 8:

Random drawing of triplets of reference images so as to obtain an "anchor" image, a "positive" image (that is, corresponding to the same model as the anchor image), a "negative" image;

Calculation for each anchor, positive and negative image of representative vectors by means of the third neural network CNN3;

Calculation of the function of loss of triplet ("triplet loss") as follows:

$$\text{Loss} = \Sigma_{i=1}^{N} [\|f_i^a - f_i^p\|_2^2 - \|f_i^a - f_i^n\|_2^2 + \alpha]$$

with $f_i^a$ the anchor image, $f_i^p$ the positive image, $f_i^n$ the negative image and $\alpha$ a given margin between two positive pairs and two negative pairs;

Updating of the weights of the third neural network CNN3 so as to distance the representative vector of the negative image from that of the anchor image and bring the representative vector of the positive image closer.

It is evident with this function that a distance between an anchor image and a positive image and a distance between an anchor image and a negative image is accumulated at the same time.

The advantage of using this loss function is that it classifies the images together and not only compares them.

During training of the third neural network CNN3 the representative vectors of each reference implant of the annotated database are calculated (step E33) and saved (step E34).

In addition, training of the third neural network CNN3 can comprise a trimming step (step E30) of each radiographic reference image. This trimming step uses the regions of reference interests stored in the database of annotated data BDD1. Therefore, a radiographic reference image is trimmed according to the corresponding region of interest. This trimming better identifies the reference implant in the reference image.

In addition, training of the third neural network can comprise a resampling step (step E31) of the reference images. This step ensures that enough implants are fairly represented and that because of this there are no types of over-represented implants.

In addition, training of the third neural network can comprise a step for augmenting data (step E32). This step is similar to that performed (step E10) for training of the first neural network CNN1.

Steps E30, E31 and E32 can be performed all together, or not.

The interest of the third neural network CNN3 is to be able to calculate similarities image by image directly, without passing through an intermediate step for predicting technical characteristics. It is therefore possible to distinguish much finer variations which are not explained via technical characteristics specific to the implants. In this way, implants which have identical own technical characteristics can be distinguished. Yet it should be noted that it is necessary to have at least one image in the annotated database $BDD_1$.

Steps E20/E30, E21/E31, E22/E32 can be performed independently for the second neural network or networks CNN2$i$ and for the third neural network.

The interest in combining these approaches at the same time (and taking metadata into account) is therefore having a more robust system which capitalizes on the advantages of each approach and which better supports extreme cases: implants having the same technical characteristics, rare implants with no or few reference images, etc.), old implants or distributed in certain countries only, etc.

The Classification Process

Figure 9:
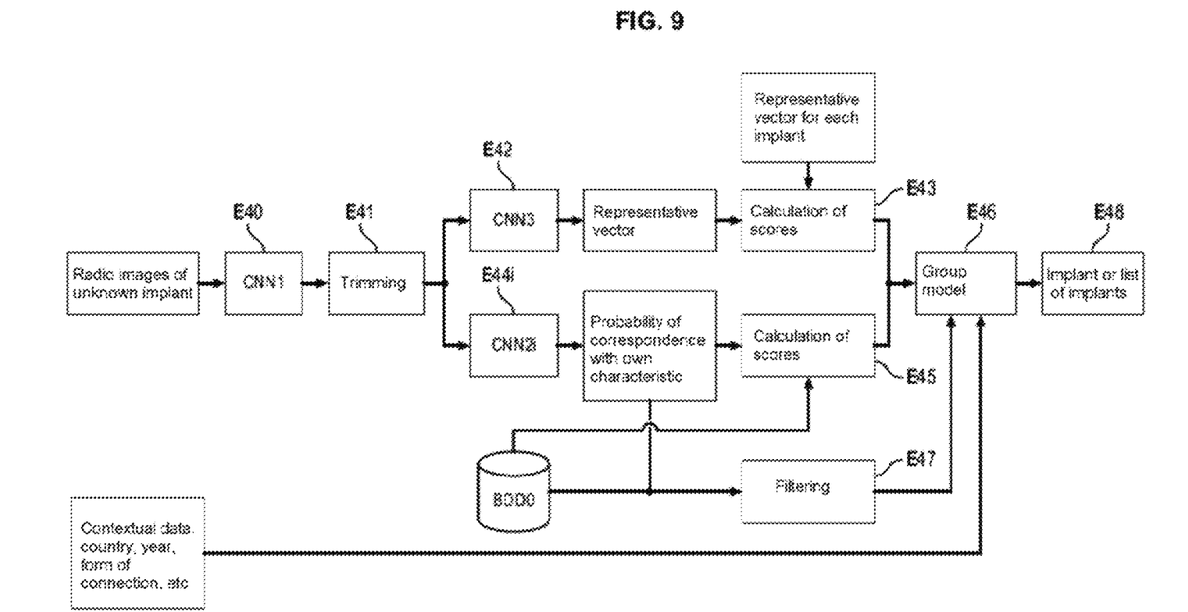
FIG. 9 illustrates steps of a process for classification of a radiographic image of a dental implant according to an embodiment of the invention.

In relation to FIG. 9, the classification process inputs a radiographic image of an unknown implant to be identified, and optionally contextual data relative to the implant which form some of the technical characteristics specific to an implant: form of the connection of the implant, year of construction of the implant, country where the implant is placed, town where the implant is placed.

By means of the first neural network CNN1, a region of interest containing the unknown implant to be detected is determined (step E40). Then the radiographic image according to this region is trimmed (step E41).

Next, the second and third neural networks are utilized at the same time or either the second neural networks only, or the third neural networks only.

By means of each second neural network CNN2$i$, determination of at least one probability of corresponding to a technical characteristics specific to an implant is made (step E44$i$).

Next, comparison of each probability of corresponding to a technical characteristic specific to an implant with a set of intrinsic technical characteristics of reference implants (these characteristics are stored in the database of reference implants $BDD_O$) is performed so as to obtain a correspondence score of technical characteristics for each reference implant (step E45). In this way, it can be evaluated which reference implant the unknown implant resembles. For example, if the predictions of each second neural network give: flared neck (99%), straight body (97%), flat tip (98%), the implants having a straight flared neck and flat tip will have a correspondence score close to 100%.

A representative vector describing the radiographic image is determined by means of the third neural network CNN3 (step E42).

The representative vector determined in this way is compared to the representative vectors of each reference implant obtained during learning of the third neural network (CNN3) so as to obtain a set of scores of similarities, each similarity score characterizing a distance of the representative vector determined at each representative reference vector (step E43). This concerns a distance between the unknown representative vector of the implant from those of reference implants, therefore known.

Next, the similarity and correspondence scores are combined to obtain scores associated with each reference implant (step E46) based on a group model. The group model can be a simple linear combination (for example an average) of the similarity and correspondence scores. Also, a simple learning model (linear regression, decision-making tree forest, in English "random forest" type, etc.) or else another neural network can be utilized for calculating this score. Such a model inputs the similarity and correspondence scores, and provides at output the overall group score. It is clear that classification may or may not comprise steps E40 and E41 such that steps E42 and E44$i$ input the trimmed radiographic image or not.

In addition, according to the contextual data available, the database of implants can be filtered (step E47) so as to retain some implants only.

On completion of step E46 only a certain number of implants is retained so as to provide a list of candidate implants (step E48).

Figure 10:
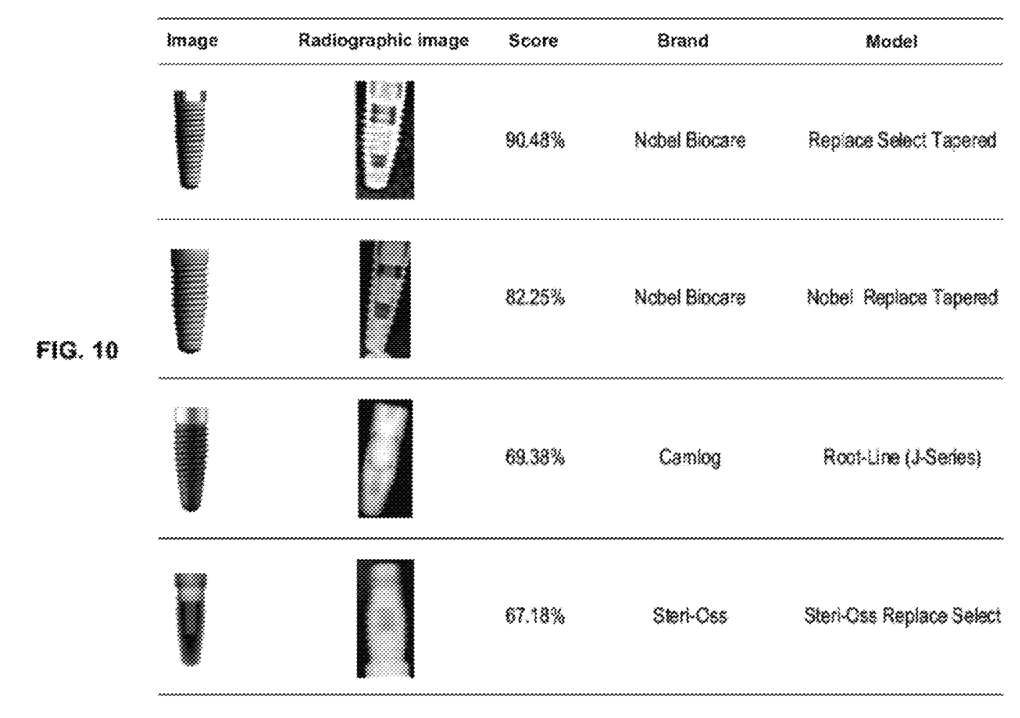
FIG. 10 illustrates an example of a list of dental implants obtained by means of a process for identification according to the invention.

It is this list of candidate implants which the practitioner can consult for detection. FIG. 10 illustrates an example of a list of candidate implants which can be supplied to a practitioner. This list comprises an image of a reference implant, the corresponding radiographic image as well as a correspondence score (obtained at step E46), the brand and the model in the brand.

The invention claimed is:

1. An identification process (ID) of a dental implant, optionally worn by an individual, comprising the following steps, performed by a processing unit:
   obtaining (OBT) a radiographic input image in which a dental implant is visible;
   classifying (CLASS) a region of interest of the radiographic input image, the step of classifying comprising
      detecting a region of interest of the radiographic image by means of a first neural network (CNN1)
      trimming the radiographic image according to this region of interest,
      the first neural network having been trained from a database of annotated data and radiographic reference images, said database of annotated data ($BDD_1$) comprising references of reference implants and coordinates of reference regions of interest of the radiographic reference images
      determining at least one probability of corresponding to a technical characteristic specific to an implant, each probability being determined by means of a second neural network (CNN2$i$);

comparing each probability of corresponding to a technical characteristic specific to an implant with a set of technical characteristics of reference implants so as to obtain for each reference implant a correspondence score determining a representative vector by means of a third trained neural network (CNN3), the representative vector describing the radiographic image optionally trimmed according to the region of interest comparing the determined representative vector with a set of representative reference vectors corresponding to reference implants obtained during a learning step of the third neural network (CNN3) so as to obtain a set of scores of similarities, each score characterizing a distance of the representative vector determined at each representative reference vector implants obtained during a learning step of the third neural network (CNN3) so as to obtain a set of scores of similarities, each score characterizing a distance of the representative vector determined at each representative reference vector the second and third neural networks are utilized at the same time for obtaining in parallel the set of scores of similarities; the classification further comprising combing the similarity and correspondence scores for obtaining scores associated with each reference implant;

obtaining a list of candidate implants to be the dental implant visible on the radiographic input image, the list being ordered as a function of a probability of being the implant visible on the radiographic input image.

2. The process according to claim 1, comprising a step of determining from the set of scores of similarities and/or the correspondence score associated with each reference implant of a set of final scores associated with each reference implant, each score quantifying the correspondence between the implant visible on the image and each reference implant and constituting the list of candidate implants (E48).

3. The process according to claim claim 1, wherein the reference implants originated from a database of implants (BDD$_0$) optionally filtered as a function of contextual data such as for example the origin of the implant, the year of construction, the form of connection.

4. The process according to claim 1, comprising a learning step (APP) of at least one neural network from a database of annotated data (BDD$_1$) and radiographic reference images, said database of annotated data (BDD$_1$) comprising references of the reference implants and coordinates of reference regions of interest of the radiographic reference images, the step of learning (APP) identifying on the reference images a region of interest and technical characteristics specific to each reference implant visible on each reference image and vectors representative of each reference image.

5. The process according to claim 4, wherein the learning step (APP) of at least one neural network comprises a step for augmenting data consisting of applying to each radiographic reference implant image at least one random transformation from the following transformations: rotation, trimming, enlarging, modification of brightness, modification of contrast, mirror, perspective, noise.

6. The process according to any claim 4, wherein the learning step (APP) comprises the learning of the first neural network (CNN1) from the database of annotated data (BDD$_1$) such that for a radiographic reference image in which an implant is visible the first neural network (CNN1) is configured to determine coordinates of a region of interest containing said implant.

7. The process according to claim 4, wherein the learning step (APP) comprises the learning of the third neural network (CNN3) from the database of annotated data (BDD$_1$) such that the third neural network (CNN3) is configured to determine a representative vector describing the radiographic image.

8. The process according to claim 4, wherein the learning step (APP) comprises the learning of an entire second neural network from the database of annotated data (BDD$_1$) such that each neural network of the entire second neural network is configured to determine a probability of corresponding to a technical characteristic specific to an implant.

9. The process according to claim 4, wherein the learning step (APP) of the entire second neural network and of the third neural network comprises a step for trimming the reference images according to the identified regions of interest.

10. The process according to claim 4, wherein the learning step (APP) of the entire second neural network and of the third neural network (CNN3) comprises a resampling step to ensure that the technical characteristics specific to each implant are fairly represented.

11. Non-transitory computer-readable medium comprising code instructions for executing a process (ID) according to claim 1.

* * * * *